United States Patent
Das et al.

(10) Patent No.: US 6,367,961 B1
(45) Date of Patent: Apr. 9, 2002

(54) APPARATUS FOR MAKING AN EMULSION

(75) Inventors: Wilfred Das, Gurnee; Randall M. Farmer, Mundelein; John McDonald, Libertyville; Steven G. Meyers, Lake Zurich, all of IL (US)

(73) Assignee: Abbott Laboratories, Aboott Park, IL (US)

( * ) Notice: Subject to any disclaimer, the term of this patent is extended or adjusted under 35 U.S.C. 154(b) by 0 days.

(21) Appl. No.: 09/220,426

(22) Filed: Dec. 24, 1998

(51) Int. Cl.[7] .............................. B01F 5/06; A61L 2/16; F04B 23/00
(52) U.S. Cl. .................... 366/176.3; 422/294; 422/295; 417/313; 417/441
(58) Field of Search .............................. 516/20, 21, 53, 516/924; 366/138, 160.4, 176.1, 176.2, 176.3; 422/26, 33, 292, 294, 295; 417/568, 539, 313, 441; 137/241

(56) References Cited

U.S. PATENT DOCUMENTS

| | | | | |
|---|---|---|---|---|
| 3,180,273 A | * | 4/1965 | Loliger | 417/313 |
| 3,253,882 A | * | 5/1966 | Deackoff | 417/539 |
| 4,081,863 A | * | 3/1978 | Rees | 366/176.1 |
| 4,773,833 A | * | 9/1988 | Wilkinson et al. | 417/539 |
| 5,273,407 A | * | 12/1993 | Jarchau et al. | 417/539 |
| 5,403,169 A | | 4/1995 | Yokoi et al. | 417/568 |
| 5,411,380 A | * | 5/1995 | Bristol et al. | 417/454 |
| 5,746,728 A | | 5/1998 | Py et al. | 604/298 |

FOREIGN PATENT DOCUMENTS

| | | |
|---|---|---|
| DE | 4007832 | 9/1990 |
| DE | 4134882 | 12/1992 |
| NL | 0137650 | 6/1973 |

OTHER PUBLICATIONS

PTO 01–114, Translation of DE 41 34 882 A1 (USPTO, Wash, DC, Oct. 2000).*
European Search Report dated Jun, 2, 2000 fo International application PCT/US99/30596, ISA/EP, Haag, NL. pp. 1–4, Jun. 2000.*

* cited by examiner

Primary Examiner—Daniel S. Metzmaier
(74) Attorney, Agent, or Firm—Brian R. Woodworth

(57) ABSTRACT

An apparatus for making a sterile emulsion, comprising a fluid pathway, a pumping bore, a reciprocable (reciprocal) member, and a valve body. The pumping bore being in fluid communication with the fluid pathway and having a reciprocable member reciprocably disposed in the pumping bore. The reciprocable member having first portion disposed in fluid communication with the fluid pathway and a second portion isolated from the fluid pathway, said second portion having a sterilant passage adjacent thereto. The fluid pathway, reciprocable member first portion and reciprocable member second portion may be sterilized and one or more emulsion constituents may be directed into the fluid pathway defined by the piston apparatus after sterilization. The valve body defines a valve bore in communication with the fluid pathway and a valve plunger disposed therein. The valve body may also be configured to maintain emulsion sterility.

8 Claims, 5 Drawing Sheets

… …

APPARATUS FOR MAKING AN EMULSION

TECHNICAL FIELD

The present invention relates generally to a process for making an emulsion, and more particularly to a process for making a sterile emulsion which employs an improved homogenizer having a piston configured to maintain the sterility of the emulsion during production. The present invention further relates to an improved valve block having a movable valve plunger, the valve block configured to maintain the sterility of an emulsion produced thereby.

BACKGROUND OF THE INVENTION AND TECHNICAL PROBLEMS POSED BY THE PRIOR ART

Various techniques have been developed for the production of sterile therapeutic compounds and the like, including solutions, emulsions, and other liquids. Such techniques include sterile filtration and heat-processing. While these techniques are in widespread practice, they are not suitable for the production of all types of compounds. Experience has shown that for production of certain sterile emulsions, sterile filtration may not be effective in obtaining the desired level of sterility, while heat processing is unsuitable for certain heat-labile compounds.

The production of emulsions typically entails the use of a homogenizer which effects particle or globule size reduction in a mixture of two immiscible liquids. Such particle size reduction is effected by pressurization of a mixture to relatively high pressures, e.g., 7,000–20,000 psi, or more, followed by direction of the pressurized mixture through a valve assembly defining an appropriately sized orifice by which the mixture is accelerated to high velocities for impingement upon a particle-reducing surface, sometimes referred to as an impact ring. Operation of such homogenizers effects the desired particle size reduction for emulsion production.

A typical homogenizer includes one or more reciprocably operated pump pistons which act to pressurize the mixture of components from which the emulsion is formed. Such an apparatus also typically includes a valve assembly, including a valve plunger which can be adjusted for controlling the size of an orifice through which the pressurized mixture is directed. O-rings of known construction are used in connection with the pump pistons and valve plungers in order to seal the interior fluid pathway of the homogenizer from an external environment thereof.

Steam sterilization ("SIP", i.e., steam in place) has been shown to be an effective method for sterilizing the fluid pathway defined by the homogenizer. Steam sterilization also effectively sterilizes those portions of the pump piston and adjustable valve plunger that are exposed to the steam. However, by virtue of the configuration of the typical homogenizer, a portion of the reciprocating pump piston, as well as a portion of the adjustable valve plunger, move between positions that are internal and external to the fluid pathway, i.e., between sterile and non-sterile environments. As a consequence, reciprocation of the pump piston, or adjustment of the valve plunger, can result in microbial ingress into the fluid pathway, potentially adversely affecting sterility of the emulsion being produced by the homogenizer. While it is possible to operate a homogenizer apparatus in a "clean room" environment and thereby obviate the potential for microbial ingress, such a solution is both costly and cumbersome.

The present invention is particularly directed to a process and apparatus for forming a sterile emulsion wherein portions of the apparatus which are movable into and out of the fluid pathway of the apparatus are independently sterilized.

SUMMARY OF THE INVENTION

The present invention is directed to a process and related apparatus for the production of a sterile emulsion. The apparatus of the present invention defines a fluid pathway and a pumping bore where the pumping bore is in fluid communication with the fluid pathway. A reciprocable member having a first portion and a second portion is mounted such that the first portion is in fluid communication with the fluid pathway and such that the second portion moves into and out of fluid communication with the fluid pathway. The apparatus defines a sterilant passage constructed to deliver sterilant to a portion of the pumping bore adjacent to the second portion of the reciprocable member. In one embodiment of the present invention, the apparatus includes a wall defining a chamber therein, the wall being constructed to seal the reciprocable member from an external environment of the wall. The chamber defined by the wall is in fluid communication with the pumping bore.

The present invention also is directed to a valve body that defines a bore in fluid communication with the fluid pathway of a homogenizer. A valve plunger having a first portion and a second portion is mounted such that the first portion is in fluid communication with the fluid pathway and such that the second portion can be moved into and out of fluid communication with the fluid pathway. The apparatus further includes an apparatus constructed to sterilize the second portion of the valve plunger, thereby preventing microbial ingress into the fluid pathway.

The present invention is further directed to a method for performing homogenization. The method includes the step of providing a homogenizing apparatus constructed in accordance with the present invention, as above-described. The method also includes the step of effecting sterilization of the second portion of the reciprocable member and the second portion of the movable member. The method further includes the step of directing one or more emulsion constituents into the fluid pathway defined by the homogenizing apparatus. Thereafter, the reciprocable member is reciprocated in order to effect homogenization under sterile conditions.

Other features and advantages of the present invention will become readily apparent from the following detailed description, the accompanying drawings, and the appended claims.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

Figure 1:
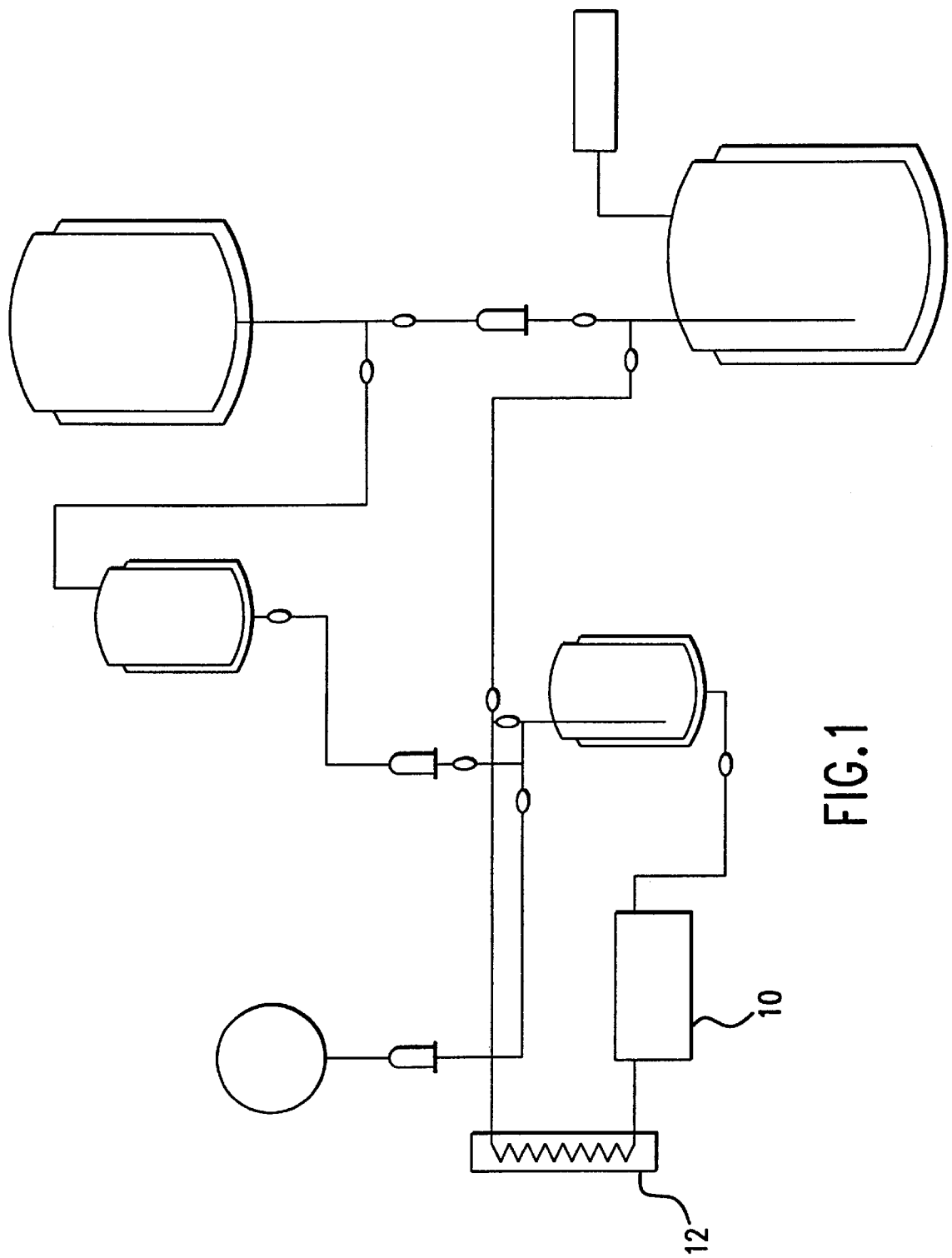
FIG. 1 is a diagrammatic view of a system for producing an emulsion that embodies the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

A system for producing an emulsion is generally depicted in FIG. 1. Although the system of the present invention was particularly developed for use in the production of a sterile emulsion useful as an ultrasound imaging agent containing dodecafluoropentane gas, it will be appreciated that the system of the present invention can be constructed and used to produce a wide variety of emulsions.

The system generally depicted in FIG. 1 has been constructed to maintain the sterility of fluids flowing therethrough, including the components of an emulsion being produced thereby, by sterile filtration of each of the components of the emulsion as they are introduced into the system. However, the system of the present invention need not provide for the sterile filtration of each component of the emulsion produced by the system. For example, it is possible that one or more of the emulsion components introduced into the system are sterile prior to their introduction into the system for processing, thereby obviating the need for further sterilization of these components. Further, the system of the present invention can be modified such that sterilization of the components of the emulsion is performed after they are introduced into the system, e.g., by heat sterilization or filtration, but before they reach the portion of the fluid pathway adjacent to the reciprocable member discussed in detail herein. Finally, it is possible that the apparatus and method of the present invention will be used in the production of a non-sterile emulsion, in which case it is not necessary to sterilize the emulsion components prior to their introduction into the homogenizing apparatus.

As shown in FIG. 1, the present system includes a homogenizer 10 which, as will be further described, effects particle or globule size reduction of one or more components of an emulsion during the formation of the emulsion. In the depicted system, a heat exchanger 12 is provided to control the temperature of the emulsion being formed, thereby avoiding degradation of the compound by excessive heating. Heat exchanger 12 can be of any known construction.

Figure 2:
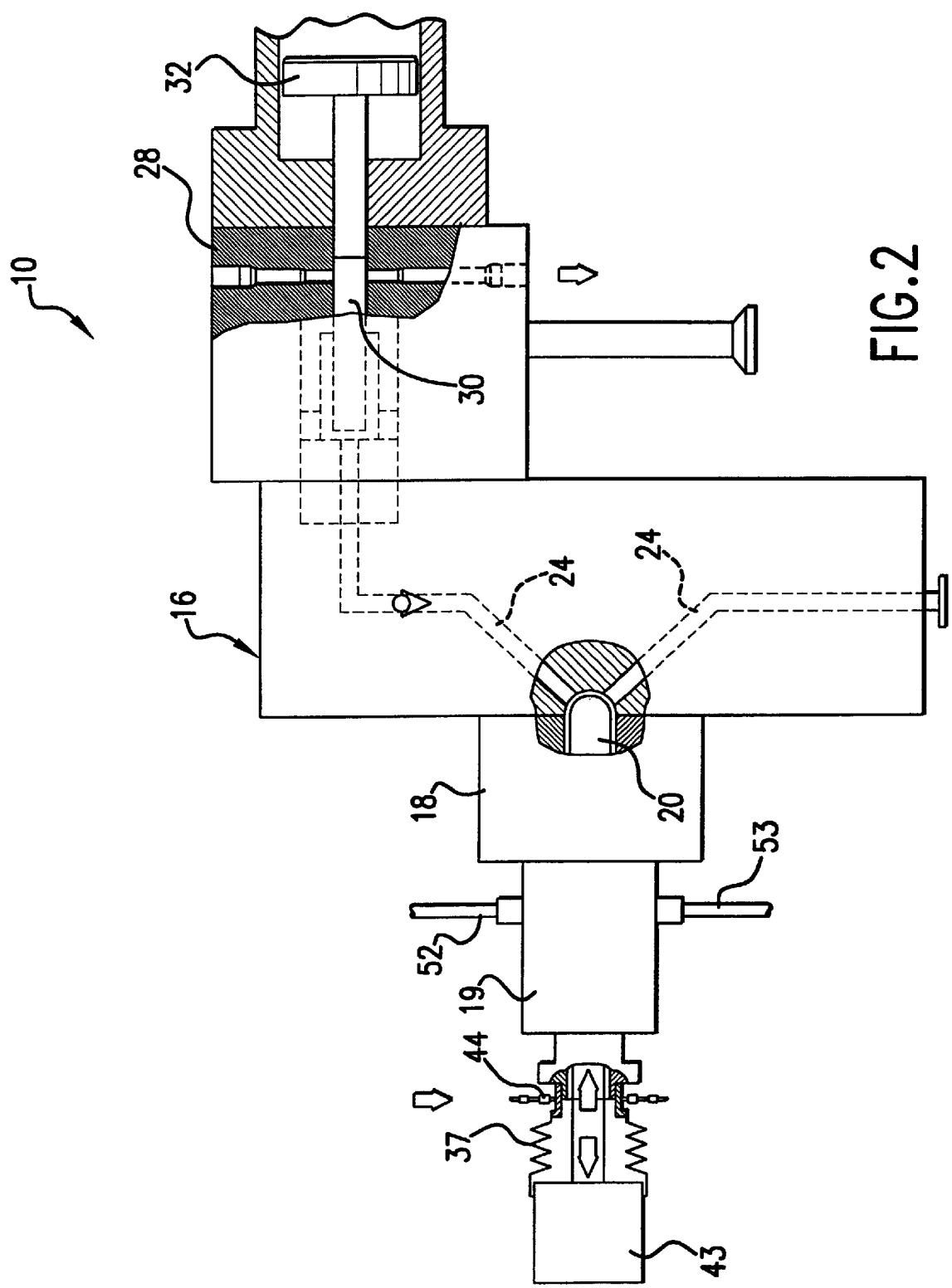
FIG. 2 is a diagrammatic view of the homogenizer apparatus of the present system.
Figure 3:
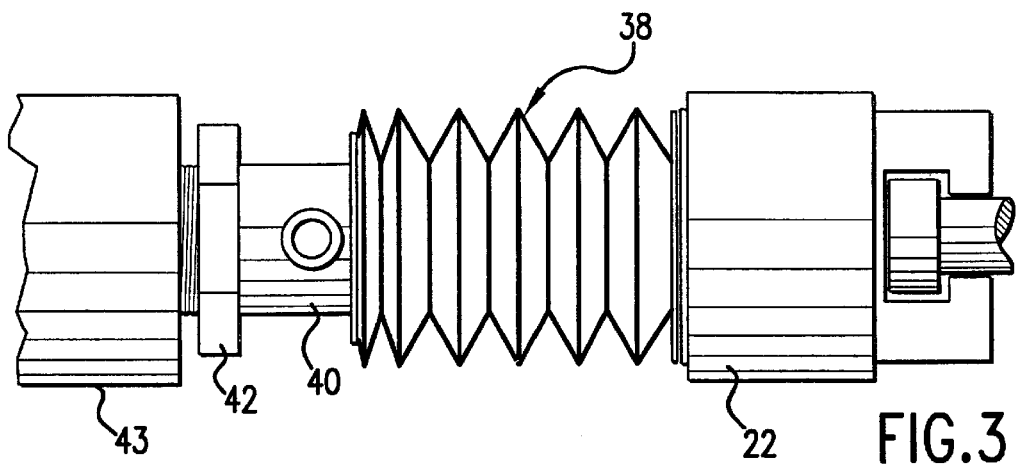
FIGS. 3, 4, and 5 are diagrammatic views of a collapsible enclosure for a reciprocable piston of the homogenizer of the present invention.
Figure 8:
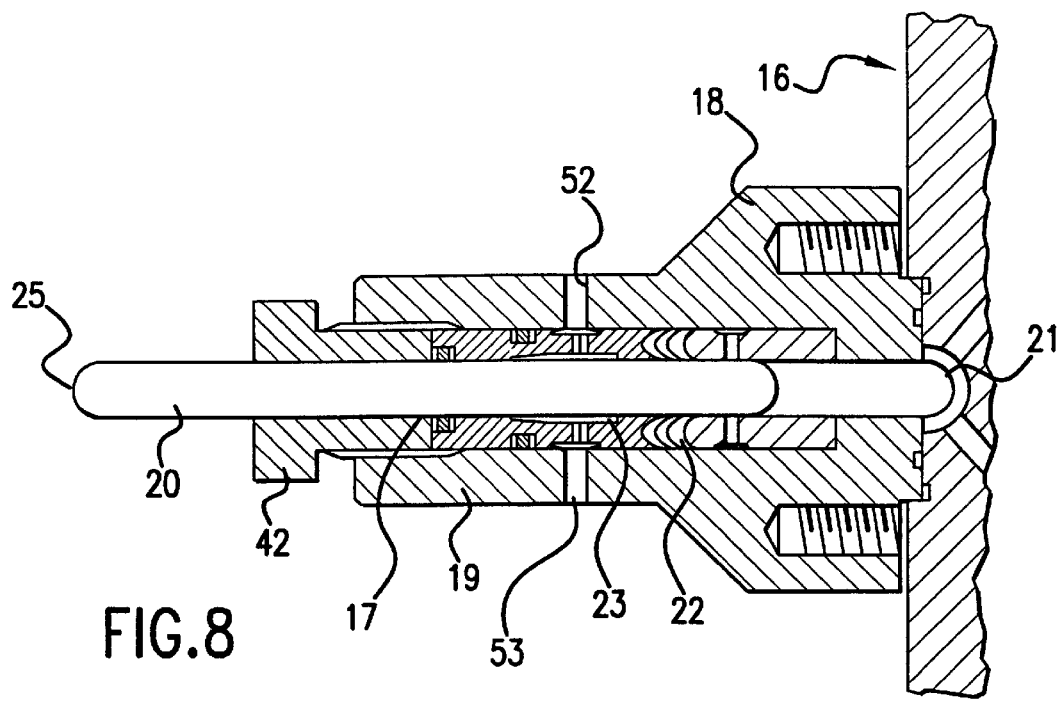
FIG. 8 is a cross-sectional view illustrating a pump piston of the homogenizer apparatus of the present invention.

Homogenizer 10 includes a homogenizer body generally depicted at 16 in FIG. 2. Homogenizer body 16 includes a piston block 18 and a homogenizer gland 19. As shown in FIG. 8, the homogenizer 10 includes at least one reciprocable member 20 which can reciprocate within a pumping cylinder or bore 17 defined by homogenizer body 16. In the depicted embodiment, pumping bore 17 is defined through piston block 18 and homogenizer gland 19. Pumping bore 17 is in fluid communication with a fluid pathway 24 which is defined through homogenizer body 16. As discussed in detail herein, emulsion components undergoing homogenization pass through fluid pathway 24 during processing (see FIG. 9).

It will be appreciated that the system of the present invention can include more than one reciprocable member 20. For example, in one contemplated embodiment of the present invention, three (3) reciprocable members 20 act in concert with one other in order to produce the desired characteristics of the emulsion produced by the system. The number, size, and orientation of reciprocable members 20 is considered to be a matter of design choice that is determined by the nature of the emulsion to be produced, as well as the characteristics of the components of that emulsion.

Figure 4:
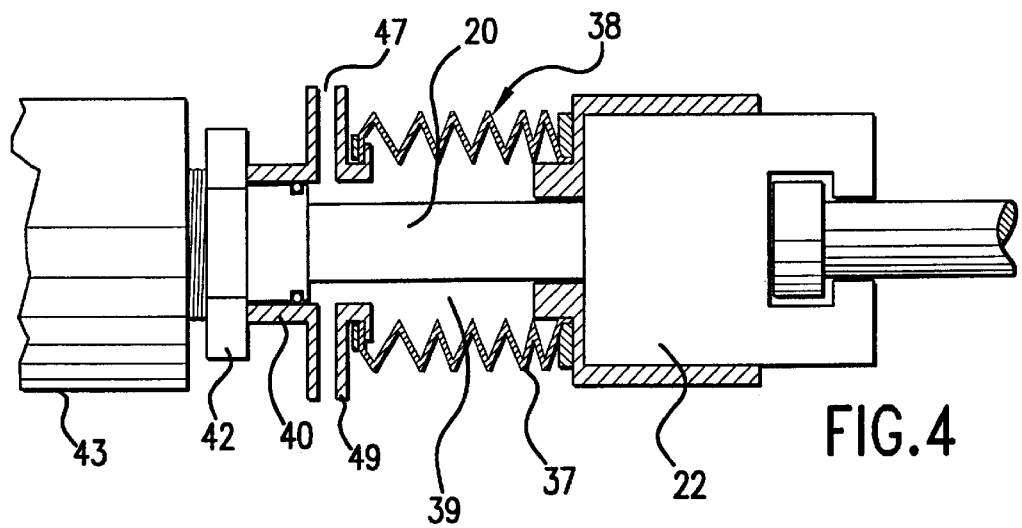
Figure 5:
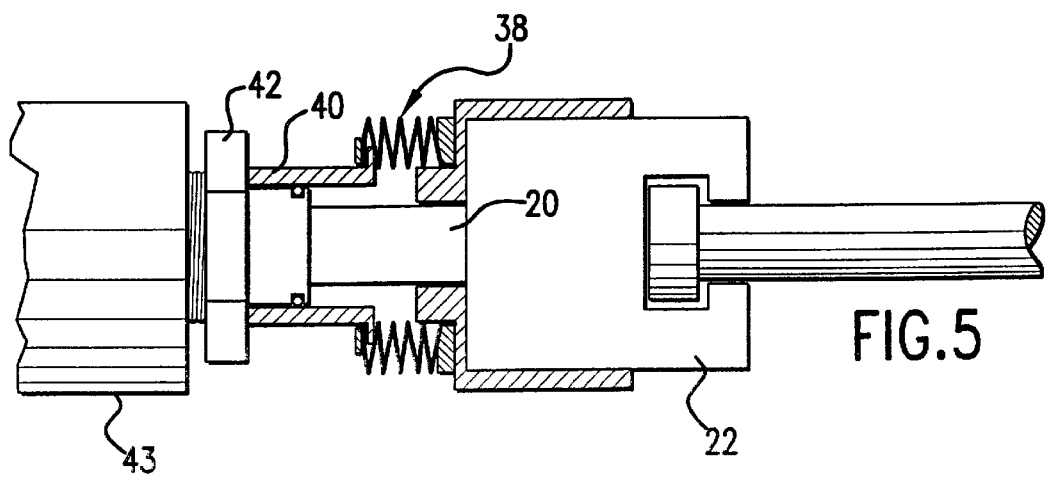
Figure 6:
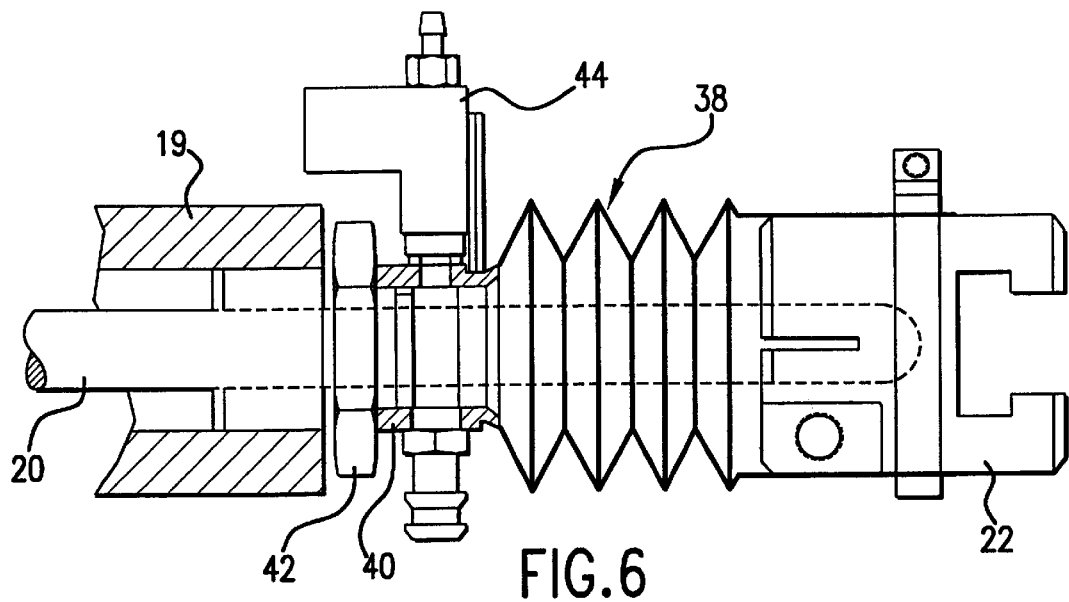
FIG. 6 is a diagrammatic view of an atomizer for atomizing sterilant directed against a second portion of the reciprocable piston.

Reciprocable member 20 is reciprocally driven by a driver 43 operatively connected thereto as depicted in FIGS. 4 and 5. Driver 43 can be any of a variety of known mechanisms for operating a piston, including, but not limited to, suitable electrical, hydraulic, and mechanical motors. Driver 43 and reciprocable member 20 are constructed to generate sufficient pressure within fluid pathway 24 defined by homogenizer body 16 in order to affect the desired particle size reduction/emulsion effect. In one embodiment of the present invention, driver 43, reciprocable member 20, and pumping bore 17 are constructed to generate a pressure of approximately 7,000 psi to approximately 20,000 psi within fluid pathway 24. It will be appreciated that the pressures necessary to operate optimally a system constructed in accordance with the present invention will be dictated by the characteristics of the components of the emulsion and the emulsion itself, as well as the other operating parameters of the system.

Ingredients pressurized as a result of the reciprocation of reciprocable member 20 are forced through fluid pathway 24 to a valve body 28 associated with homogenizer body 16. A valve plunger 30 is positioned within the valve body 28 such that it is movable. The valve plunger 30 coacts with the valve body 28 to define an orifice, generally indicated at 34, through which pressurized emulsion components are directed. The position of valve plunger 30 relative to valve body 28 preferably is adjustable, e.g., by way of a pneumatic or threaded adjustment of known construction and operation, in order to adjust the size of orifice 34. In the embodiment depicted in the accompanying figures, actuation face 32 is provided to facilitate adjustment of the position of valve plunger 30.

As the pressurized emulsion components in fluid pathway 24 pass through the orifice 34 (see FIG. 9), they are accelerated to a relatively high velocity because the cross-sectional area of orifice 34 is smaller than the cross-sectional area of fluid pathway 24 upstream of valve body 28. An impact ring 31 is positioned downstream of the orifice 34 such that emulsion components passing through orifice 34 are directed onto the impact ring 31. Impingement of the emulsion components on the impact ring 31 affects particle or globule size reduction of otherwise immiscible liquids, thus forming the desired emulsion. It is possible to adjust the resulting particle or globule size by adjusting the relative position of valve plunger 30 within valve body 28, thereby adjusting the size of orifice 34.

The emulsion created as a result of impingement on impact ring 31 exits fluid pathway 24 through an outlet passage 36. The resulting emulsion can be recirculated through the homogenizer for further processing, as required, in order to achieve the desired degree of particle or globule size reduction.

Reciprocable member 20 includes a first portion 21, a second portion 23, and a third portion 25, second portion 23 being positioned between first portion 21 and third portion 25. In the embodiment of the present invention depicted in the accompanying figures, first portion 21 is in constant, fluid communication with fluid pathway 24. Accordingly, first portion 21 of reciprocable member 20 can be sterilized simultaneously with the sterilization of fluid pathway 24, e.g., by steam sterilization prior to operation of the homogenizer of the present invention. However, in the embodiment of the present invention depicted in the accompanying figures, second portion 23 of reciprocable member 20 moves into and out of fluid contact with fluid pathway 24 due to the substantially fluid-tight seal between pumping bore 17 and reciprocable member 20 at packing 22. Thus, sterilization of fluid pathway 24 will not sterilize second portion 23 of reciprocable member 20 when the second portion 23 of reciprocable member 20 is on the left side of packing 22, i.e., in a second position. Nor will sterilization of fluid pathway 24 sterilize portions of pumping bore 17 on the left side of packing 22.

In the depicted embodiment of the present invention, third portion 25 of reciprocable member 20 is constantly, fluidly isolated from fluid pathway 24. However, it will be appreciated that third portion 25 may be omitted without affecting operation of the apparatus and method of the present invention.

It has been discovered that microbial ingress across packing 22 and into fluid pathway 24 can occur during reciprocation of reciprocable member 20 between first and second positions if microbes are present in the environment surrounding the second portion 23 of reciprocable member 20 when it is in its second position. It is this microbial ingress that is obviated by the apparatus of the present invention.

As used herein, the term "first position" of reciprocable member 20 is intended to refer to a position in which second portion 23 of reciprocable member 20 is positioned to the right of packing 22, i.e., where second portion 23 is in fluid communication with fluid pathway 24.

As used herein, the term "second position" of reciprocable member 20 is intended to refer to a position in which second portion 23 of reciprocable member 20 is positioned to the left of packing 22, i.e., where second portion 23 is fluidly isolated from fluid pathway 24.

It is to be appreciated that second portion 23 of reciprocable member 20 is intended to include any portion of reciprocable member 20 that passes packing 22 during reciprocation of reciprocable member 20 between the first and second positions. Second portion 23 is not intended to be limited to a discrete portion of reciprocable member 20.

Figure 9:
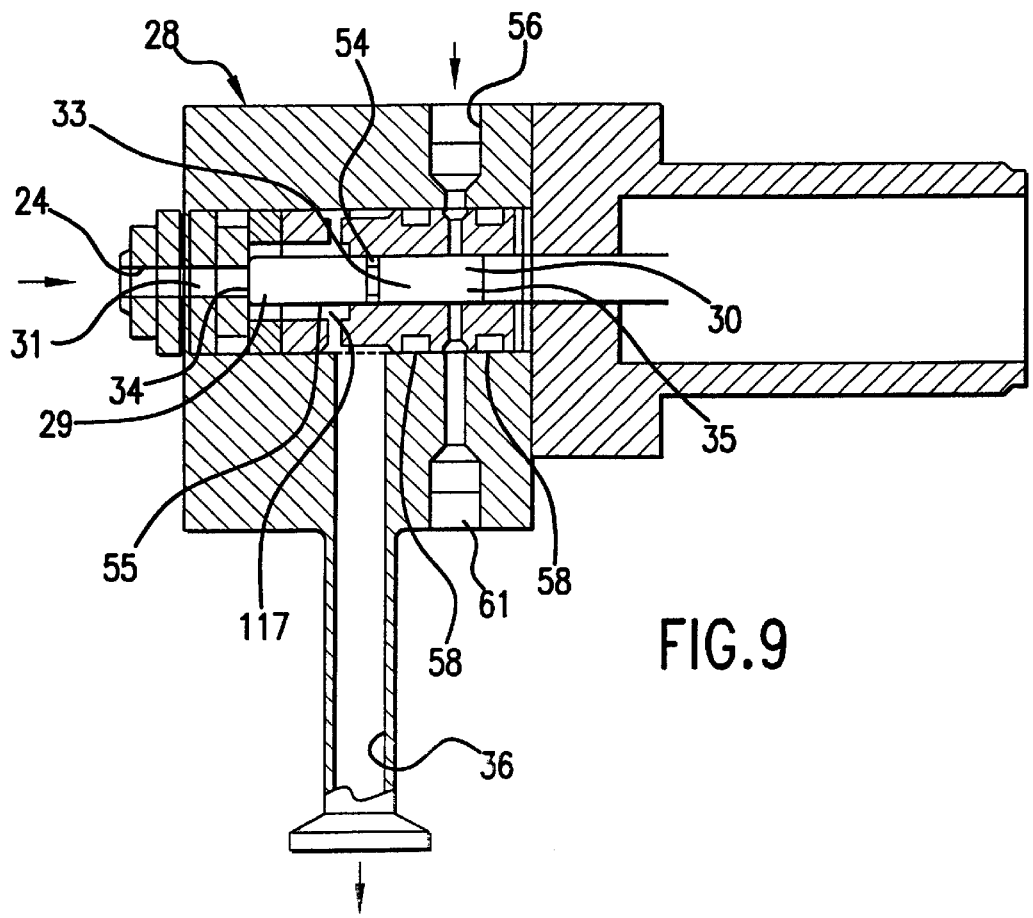
FIG. 9 is a cross-sectional view illustrating an arrangement for supplying sterilant to a valve assembly of the homogenizer of the present invention.

Valve plunger 30 of the present invention is depicted in FIG. 9. Valve plunger 30 includes a first portion 29, a second portion 33, and a third portion 35. First portion 29 of valve plunger 30 is positioned such that it is in constant fluid communication with fluid pathway 24. Accordingly, first portion 29 of valve plunger 30 can be sterilized simultaneously with the sterilization of fluid pathway 24, e.g., by steam sterilization, prior to operation of the homogenizer of the present invention. Second portion 33 of valve plunger 30 is positioned such that it can be moved into and out of fluid communication with fluid pathway 24. Third portion 35 of valve plunger 30 is positioned such that it is never in fluid communication with fluid pathway 24.

As used herein, the term "first position" of valve plunger 30 is intended to refer to a position in which second portion 33 of valve plunger 30 is positioned to the left of O-ring seal 54, i.e., where second portion 33 is in fluid communication with fluid pathway 24.

As used herein, the term "second position" of valve plunger 30 is intended to refer to a position in which second portion 33 of valve plunger 30 is positioned to the right of O-ring seal 54, i.e., where second portion 33 is fluidly isolated from fluid pathway 24.

It is to be appreciated that second portion 33 of valve plunger 30 is intended to include any portion of valve plunger 30 that passes O-ring seal 54 during movement of valve plunger 30 between the first and second positions. Second portion 33 is not intended to be limited to a discrete portion of valve plunger 30.

Sterilization of fluid pathway 24 will not sterilize second portion 33 and third portion 35 of valve plunger 30 when valve plunger 30 is in its second position due to the substantially fluid-tight seal between valve body 28 and valve plunger 30 at O-ring seal 54. Nevertheless, it has been discovered that microbial ingress into fluid pathway 24 can occur as a result of the repositioning of valve plunger 30 if microbes are present in the environment surrounding second and third portions 33, 35 of valve plunger 30. In particular, microbial ingress can occur when second portion 33 of valve plunger 30 is moved from a position fluidly isolated from fluid pathway 24 to a position in fluid communication fluid pathway 24.

It is possible to prevent microbial ingress into fluid pathway 24 at both reciprocable member 20 and at valve plunger 30 by isolating them from their respective external environments and by ensuring that they remain sterile throughout operation of the homogenizer of the present invention. Thus, in accordance with the present invention, an arrangement is provided for effecting a secondary or localized sterilization of the reciprocable member 20 and the valve plunger 30 by directing a sterilant against the portions thereof that are movable into and out of fluid contact with fluid pathway 24, i.e., second portion 23 of reciprocable member 20 and second portion 33 of valve plunger 30.

The arrangement for effecting secondary or localized sterilization of second portion 23 of reciprocable member 20 will now be described. A wall 37 defining a chamber 39 is provided on homogenizer body 16. Wall 37 is constructed so as to isolate reciprocable member 20 from an external environment of wall 37 while simultaneously allowing reciprocable member 20 to be reciprocable within pumping bore 17. In addition, wall 37 also isolates pumping bore 17 from the external environment of wall 37. Chamber 39 is in fluid communication with pumping bore 17. In the embodiment of the present invention depicted herein, wall 37 is a collapsible enclosure in the form of a collapsible bellows member 38.

Pump driver 43 is constructed to impart reciprocal motion to reciprocable member 20 between its first and second positions. Pump driver 43 can have a variety of known configurations, including, for example, electronic, mechanical and pneumatic motors. Pump driver 43 can be disposed within wall 37, i.e., in chamber 39. However, in the embodiment of the present invention depicted in the accompanying figures, pump driver 43 is mechanically connected to bellows member 38 such that reciprocating motion can be imparted by pump driver 43 to reciprocable member 20. Bellows member 38 extends between pump driver 43 and a sleeve 40 fitted to a packing nut 42 mounted on homogenizer body 16. Bellows member 38 in this embodiment expands and contracts upon operation of pump driver 43, i.e., upon reciprocation of reciprocable member 20, thereby allowing reciprocation of reciprocable member 20 within pumping bore 17.

In order to sterilize second portion 23 of reciprocable member 20 prior to operation of the homogenizer of the present invention, and thereby prevent microbial ingress into fluid pathway 24 from second portion 23 during operation of the homogenizer, a sterilant can be directed into the chamber 39 defined by wall 37 when reciprocable member 20 is in its second position. As depicted in FIG. 2, an atomizer 44 is fluidly connected to chamber 39.

Atomizer 44 is constructed to deliver an atomized sterilant to chamber 39, to second portion 23 of reciprocable member 20, and to the portions of pumping bore 17 adjacent to second portion 23. It will be appreciated, however, that sterilant can be introduced into chamber 39, and thus to second portion 23 and to portions of pumping bore 17 adjacent thereto, at any number of positions. Further, it will be appreciated that an atomized sterilant is not required in order to effect the desired sterilization of second portion 23 of reciprocable member 20. For example, atomizer 44 can be disposed so as to provide a sterilant, e.g., hydrogen peroxide ($H_2O_2$), in atomized form in chamber 39 during operation of the homogenizer 10 through sterilant inlet 47 on sleeve 40, thereby sterilizing second portion 23 of reciprocable member 20 and the portions of pumping bore 17 adjacent thereto.

Figure 7:
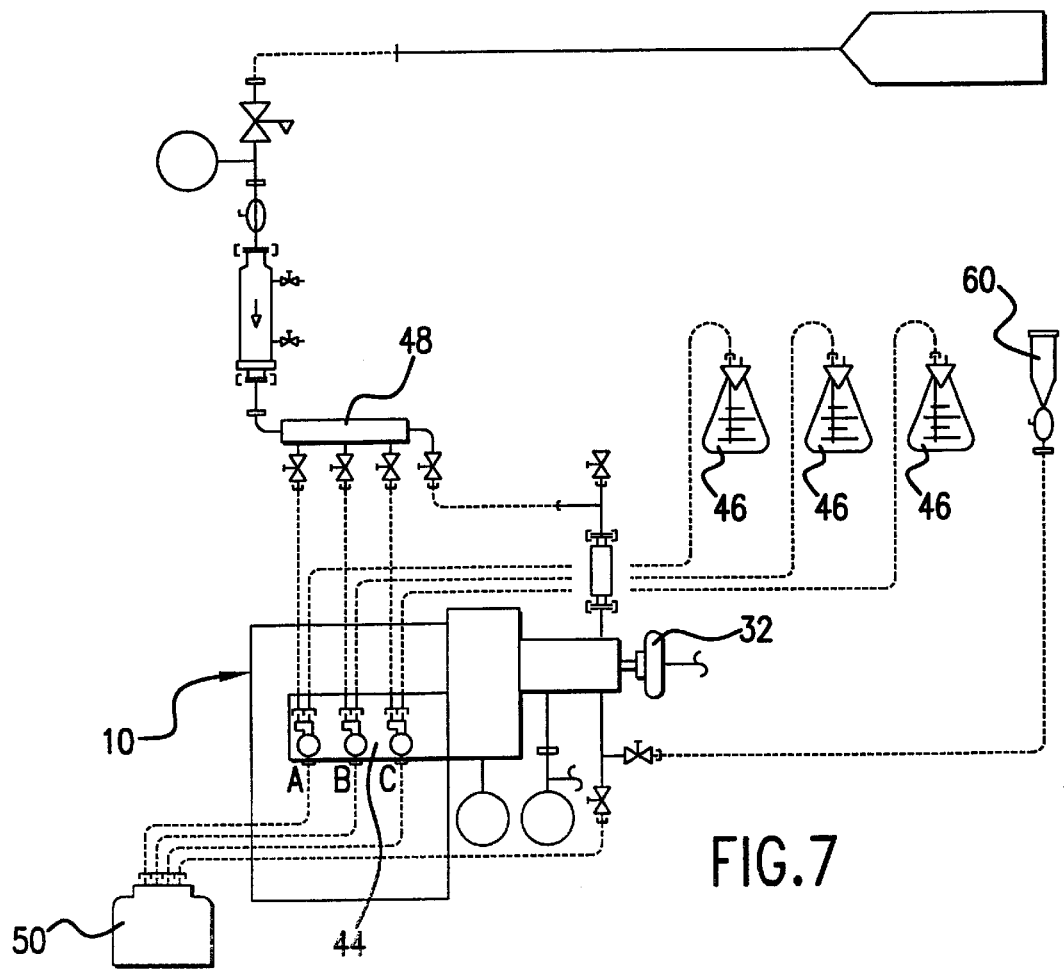
FIG. 7 is a diagrammatic view illustrating an arrangement for directing sterilant to the homogenizer apparatus of the present invention.

FIG. 7 diagrammatically illustrates an arrangement for supplying sterilant to the interior environments defined by three walls 37 in a homogenizer system having three reciprocable members 20. A plurality of sterilant reservoirs 46, each containing a sterilant e.g., hydrogen peroxide, are respectively connected to a plurality of atomizers 44 respectively associated with three reciprocating members 20 (generally designated A, B, C) of homogenizer 10. An air header 48 supplies sterile gas, e.g., sterile air or nitrogen, to the atomizers. After the sterilant has been introduced into chamber 39, it is allowed to exit through sterilant outlet 49. Sterilant exiting through sterilant outlet 49 is collected in a waste reservoir 50.

The sterility of the reciprocable member 20 is maintained, after the delivery of sterilant into the interior environment of wall 37, by maintaining the interior environment of wall 37 under positive pressure during operation of the homogenizer 10. In the depicted embodiment, sterile gas, e.g., sterile air or nitrogen, from air header 48 is used to provide the desired positive pressure in chamber 39. In the event that bellows member 38, or some other collapsible form of wall 37, is used, it is necessary to provide for the release of sterile gas from within chamber 39 as bellows member 38 is compressed and for the introduction of sterile gas into the bellows member 38 as it is being expanded. Introduction and release of gas can be performed through one or more orifices defined between the interior and exterior environments of wall 37. In one example, gas is introduced into chamber 39 through sterilant inlet 47 and gas is released from chamber 39 through sterilant outlet 49.

In one embodiment of the present homogenizer, homogenizer body 16 defines a primary sterilant passage 52 which communicates directly with pumping bore 17. Sterilant passage 52 is fluidly connected to, or fluidly connectable to, a source of sterilant (not shown). Sterilant passage 52 delivers sterilant, e.g., steam or hydrogen peroxide, to pumping bore 17 and second portion 23 of reciprocable member 20 in order to effect sterilization thereof. Primary sterilant exit port 53 is provided in order to remove sterilant from pumping bore 17.

The arrangement for effecting sterilization of second portion 33 of valve plunger 30 will now be described. As above-discussed, O-ring seal 54 provides a fluid-tight fit between valve plunger 30 and valve body 28, thereby fluidly isolating the right side of valve plunger 30 from fluid pathway 24. In the embodiment of the present invention depicted in FIG. 9, first portion 29 of valve plunger 30 is positioned to the left of O-ring seal 54 and is in fluid communication with fluid pathway 24. Second portion 33 and third portion 35 of valve plunger 30 are positioned to the right of O-ring seal 54.

It has been discovered that microbes present on the second portion 33 of valve plunger 30 can migrate across O-ring seal 54 when the position of valve plunger 30 is altered from the second position to the first position, thereby contaminating fluid pathway 24. Accordingly, it is the further purpose of the present invention to prevent microbial migration into fluid pathway 24 across O-ring seal 54 in valve body 28.

Sterilant passages 56, 61 are defined by the valve body 28 and provide fluid communication between an external environment of valve body 28 and valve bore 55 to the right of O-ring seal 54. Sterilant, e.g., hydrogen peroxide, is directed from a sterilant source (not shown) into sterilant passages 56, 61 and into valve bore 55 (to the right of O-ring seal 54). Sterilant in valve bore 55 is thereafter released through sterilant passages 56, 61. It will be appreciated that separate inlet and outlet passages can be provided for the introduction and removal of sterilant from valve bore 55.

The release of sterilant from valve bore 55 can be facilitated by the introduction of a sterile gas, e.g., sterile air, into valve bore 55 through a port, e.g., sterilant inlet passage 56. It may also be preferable to maintain positive pressure on the right side of O-ring seal 54 during operation of the homogenizer of the present invention in order to prevent microbial ingress into valve bore 55. One or more O-rings 58 can be employed to facilitate maintenance of the desired positive gas pressure in the appropriate portion of valve bore 55.

FIG. 7 illustrates the arrangement for providing sterilant to sterilant passages 56, 61 of the valve body 28 of the homogenizer 10. A sterilant container 60 operates through a suitable valve apparatus to permit introduction of sterilant into the passages 56, 61 and thus into valve bore 55. After the desired holding period for the sterilant within valve bore 55, the sterilant is directed through passages 56, 61 and into waste reservoir 50. If desired, sterile gas from header 48 can be used to facilitate the purging of sterilant from sterilant passages 56, 61 and valve bore 55. Sterile gas from header 48 also can be used to maintain a positive gas pressure within valve bore 55 during operation of the homogenizer of the present invention.

From the foregoing, it will be observed that numerous modifications and variations can be effected without departing from the intended spirit and scope of the novel concept of the present invention. It is to be understood that no limitation with respect to the specific embodiments disclosed herein is intended or should be inferred. The disclosure is intended to cover, by the appended claims, all such modifications that fall within the scope of the claims.

What is claimed is:

1. An apparatus for making an emulsion, said apparatus comprising:
   a body defining a fluid pathway and a pumping bore therein, said pumping bore in fluid communication with said fluid pathway;
   a reciprocable member disposed in said pumping bore, said reciprocable member having a first portion and a second portion, said first portion disposed in fluid contact with said fluid pathway defined by said body, said reciprocable member being reciprocable between a first position and a second position, said second portion being in fluid contact with said fluid pathway when said reciprocable member is in said first position, said second portion being fluidly isolated from said fluid pathway when said reciprocable member is in said second position, wherein the reciprocable member and pumping bore are capable of generating a pressure sufficient for making an emulsion;

said body further defining a sterilant passage constructed to permit introduction of sterilant into a portion of said pumping bore adjacent to said second portion of said reciprocable member when said reciprocable member is in said second position;

a collapsible wall defining a chamber, said chamber in fluid communication with said pumping bore, said wall fluidly isolating said reciprocable member from an external environment of said wall; and a valve body defining a valve bore in fluid communication with said fluid pathway and a valve plunger positioned within said valve bore.

2. An apparatus in accordance with claim 1, wherein said wall is constructed to retain a positive pressure within said chamber.

3. An apparatus in accordance with claim 1, wherein said apparatus further comprises an air header constructed to deliver pressurized air to said chamber defined by said wall.

4. An apparatus in accordance with claim 1, wherein said valve plunger includes a first portion and a second portion, said first portion of said valve plunger in fluid communication with said fluid pathway, said first end portion of said valve plunger and said valve body defining an orifice therebetween, said valve plunger being movable within said valve bore between a first position and a second position, said second portion of the valve plunger being in fluid communication with the fluid pathway when the valve plunger is in the first position and the second portion of the valve plunger being fluidly isolated from the fluid pathway when the valve plunger is in the second position, said valve body defining a sterilant passage between an external environment of said valve body and said valve bore to permit introduction of sterilant into the valve bore adjacent the second portion of the valve plunger when the second portion of the valve plunger is in the second position.

5. An apparatus in accordance with claim 1, wherein the reciprocable member and pumping bore are capable of generating a pressure of between 7,000 psi to 20,000 psi within the fluid pathway.

6. An apparatus for making an emulsion, said apparatus comprising:

a body defining a fluid pathway and a pumping bore therein, said pumping bore in fluid communication with said fluid pathway;

a reciprocable member disposed in said pumping bore, said reciprocable member having a first portion and a second portion, said first portion disposed in fluid contact with said fluid pathway defined by said body, said reciprocable member being reciprocable between a first position and a second position, said second portion being in fluid contact with said fluid pathway when said reciprocable member is in said first position, said second portion being fluidly isolated from said fluid pathway when said reciprocable member is in said second position, wherein the reciprocable member and pumping bore are capable of generating a pressure sufficient for making an emulsion;

said body further defining a sterilant passage constructed to permit introduction of sterilant into a portion of said pumping bore adjacent to said second portion of said reciprocable member when said reciprocable member is in said second position; and a valve body defining a valve bore in fluid communication with said fluid pathway, a valve plunger positioned within said valve bore, said valve plunger having a first portion and a second portion, said first portion of said valve plunger in fluid communication with said fluid pathway, said first portion of said valve plunger and said valve body defining an orifice therebetween, said valve body defining a sterilant passage between an external environment of said valve body and said valve bore.

7. An apparatus for making an emulsion in accordance with claim 6, wherein said sterilant passage defined by said valve body is constructed to deliver sterilant to said valve bore at a position adjacent to the second portion of the valve plunger.

8. An apparatus for making an emulsion in accordance with claim 6, wherein the reciprocable member and pumping bore are capable of generating a pressure of between 7,000 psi to 20,000 psi within the fluid pathway.

* * * * *